United States Patent

Schwarz et al.

Patent Number: 5,719,269
Date of Patent: Feb. 17, 1998

[54] CHROMATOGRAPHY ADSORBENTS UTILIZING MERCAPTO HETEROCYCLIC LIGANDS

[75] Inventors: Alexander Schwarz, Brookline, Mass.; Meir Wilchek, Rehovot, Israel

[73] Assignee: BioSepra, Inc., Marlborough, Mass.

[21] Appl. No.: 577,229

[22] Filed: Dec. 22, 1995

Related U.S. Application Data

[62] Division of Ser. No. 243,861, May 16, 1994, Pat. No. 5,502,022.

[51] Int. Cl.$^6$ .................................... C07K 1/22
[52] U.S. Cl. .................... 530/415; 530/413; 530/412; 530/387.1; 502/401; 502/402
[58] Field of Search .................... 530/412, 413, 530/415, 387.1; 502/401, 402

[56] References Cited

U.S. PATENT DOCUMENTS

| | | |
|---|---|---|
| 4,381,239 | 4/1983 | Chibata et al. |
| 4,631,270 | 12/1986 | Yankeelov et al. ............... 514/15 |
| 4,701,500 | 10/1987 | Porath . |
| 4,897,467 | 1/1990 | Porath . |
| 5,141,966 | 8/1992 | Porath . |
| 5,185,313 | 2/1993 | Porath . |
| 5,215,889 | 6/1993 | Schultz .......................... 435/41 |
| 5,314,817 | 5/1994 | Schultz ....................... 435/188.5 |

FOREIGN PATENT DOCUMENTS

| | | |
|---|---|---|
| 168363 | 1/1986 | European Pat. Off. |
| 8902329 | 12/1989 | WIPO . |

OTHER PUBLICATIONS

Hu et al, Journal of Chromatography, vol. 646, pp. 31–35 (1993).

Jennissen et al, Journal of Chromatography, vol. 597, pp. 93–100, (1992).

Wu et al, Journal of Chromatography, vol. 584, pp. 35–41, (1992).

El–Kak et al, Journal of Chromatography, vol. 604, pp. 29–37, (1992).

El–Kak et al, Journal of Chromatography, vol. 570, pp. 29–41, (1991).

Oscarsson et al, Journal of Immunological Methods, vol. 143, pp. 143–149 (1991).

Oscarsson et al, Journal of Chromatography, vol. 499, pp. 235–247 (1990).

Porath et al, Chem. Macromol. Symp; vol. 17, pp. 359–371, (1988).

Street et al, J. Am. Chem. Soc., vol. 107, pp. 7669–7679, (1985).

Primary Examiner—Ponnathapura Achutamurthy
Assistant Examiner—T. D. Wessendorf
Attorney, Agent, or Firm—Heslin & Rothenberg, P.C.

[57] ABSTRACT

A pseudobioaffinity chromatography adsorbent adapted for use in selectively adsorbing immunoglobulins. In one embodiment, the adsorbent includes: (a) a solid support material; and (b) a ligand immobilized on the surface of the solid support material, said ligand being a compound of the formula

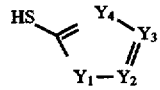

wherein $Y_1$ is selected from the group of S, $SCH_3^+$, O, NH, $NCH_3$, $CH_2$ and $CR_1R_2$ wherein at least one of $R_1$ and $R_2$ is not hydrogen; wherein each of $Y_2$, $Y_3$ and $Y_4$ is selected from the group of N, $NCH_3^+$, CH, and CR wherein R is not hydrogen; and wherein at least two of $Y_1$, $Y_2$, $Y_3$ and $Y_4$ are neither $CH_2$, CH, CR nor $CR_1R_2$.

4 Claims, No Drawings

CHROMATOGRAPHY ADSORBENTS UTILIZING MERCAPTO HETEROCYCLIC LIGANDS

This is a divisional of application Ser. No. 08/243,861 filed on May 16, 1994, now U.S. Pat. No. 5,502,022.

FIELD OF THE INVENTION

The present invention relates generally to affinity chromatography and more particularly to pseudobioaffinity chromatography.

BACKGROUND OF THE INVENTION

With the rapid development of and increasing need for monoclonal and polyclonal antibodies for both diagnostic and therapeutic purposes, research efforts have recently been directed to devising new techniques for effectively isolating antibodies from antibody-containing solutions. Some well-known, existing techniques include the use of classic liquid chromatography adsorbents, such as ion exchangers, hydrophobic supports, hydroxy apatite and gel filtration media. Unfortunately, these techniques are time-consuming and tedious to perform and cannot be applied generally to the isolation of heterogenous populations of antibodies. As a result, such techniques need to be adjusted on a case-by-case basis depending upon the specific antibody sought to be isolated.

Affinity chromatography, which relies on specific interactions between an immobilized ligand and a particular molecule sought to be purified, is another well-Known, existing technique used to purify antibodies from solution. Protein A, which is derived from the bacterium *Staphylococcus aureus*, has a strong and specific affinity for the Fc fragment of IgG antibodies and has been used for approximately one decade as an affinity ligand for purifying IgG antibodies. Protein A can be immobilized on a large variety of solid support materials, such as chromatographic beads and membranes, and can be used to obtain high purity antibodies in high yield.

Unfortunately, Protein A suffers from a number of limitations as an affinity ligand. One such limitation is the prohibitive cost of Protein A. Because of its high cost, the large scale utilization of Protein A as an affinity ligand is not often economically feasible. Another such limitation is the sensitivity of Protein A to those proteases that are commonly present in the same biological fluids (e.g., sera, ascitic fluids, milk, hybridoma cell culture supernatants, and the like) in which the antibodies being sought to be purified by affinity chromatography are also present. This sensitivity of Protein A to such proteases often leads to one or both of the following effects: (1) The recognition of Protein A towards the Fc fragments of IgG is progressively reduced; and (2) Fragments of Protein A generated by protease action contaminate otherwise pure antibody preparations.

Still another limitation with Protein A is that it is possible for Protein A to be released intact from its associated solid support material, thereby contaminating antibody preparations brought into contact therewith. The contamination of therapeutic antibody preparations with traces of Protein A or Protein A fragments is very serious not only because Protein A and/or Protein A fragments are capable of provoking an antigenic response in humans but also because Protein A is known as a potent mitogen.

Protein A is not the only protein which has been used as an affinity ligand for the purification of a class of antibodies. Protein G has similarly been used as an affinity ligand. See Bjorck et al., *J. Immunol.*, 133:969 (1984). Protein G also interacts with the Fc fragment of immunoglobulins and is particularly effective in isolating mouse IgG antibodies of class 1 (as contrasted with Protein A which is not very effective in isolating these antibodies). Protein G, however, suffers from the same types of limitations discussed above in connection with Protein A.

Recently, a third protein has been identified as an effective affinity ligand for purifying antibodies. This protein is Protein L from Peptostreptococcus magnus. Protein L, as contrasted with Protein A and Protein G, interacts specifically with the light chains of IgG antibodies without interfering with their antigen binding sites. This specificity permits Protein L to complex not only with antibodies of the IgG class but also with antibodies of the IgA and IgM classes. Despite its broad affinity, Protein L suffers from the same limitations described above in connection with Proteins A and G.

In addition to suffering from the aforementioned limitations, Proteins A, G and L are all sensitive to a number of chemical and physical agents (e.g., extreme pH, detergents, chaotropics, high temperature) which are frequently used to clean affinity chromatography columns between runs. Consequently, some people have chosen to minimize the number of cleaning cycles applied to the above-described columns so as to correspondingly minimize degradation thereto. One drawback to this tactic, however, is that failure to clean the columns regularly prevents optimal antibody purification.

Anti-antibodies represent still another type of affinity ligand used for gamma globulin purification. Anti-antibodies, however, are limited in use due to their high cost and very limited stability.

In addition to the above-described protein-based affinity ligands, there are numerous lower molecular weight pseudo-bioaffinity (i.e., less specific) ligands which have been used for antibody purification. Histidine, pyridine and related compounds represent one type of pseudobioaffinity ligand commonly used for antibody purification. See e.g., Hu et al., "Histidine-ligand chromatography of proteins: Multiple modes of binding mechanism," *Journal of Chromatography*, 646:31–35 (1993); EI-Kak et al., "Interaction of immunoglobulin G with immobilized histidine: mechanistic and kinetic aspects," *Journal of Chromatography*, 604:29–37 (1992); Wu et al., "Separation of immunoglobulin G by high-performance pseudo-bioaffinity chromatography with immobilized histidine," *Journal of Chromatography*, 584:35–41 (1992); EL-Kak et al., "Study of the separation of mouse monoclonal antibodies by pseudobioaffinity chromatography using matrix-linked histidine and histamine," *Journal of Chromatography*, 570:29–41 (1991), all of which are incorporated herein by reference. See generally U.S. Pat. Nos. 5,185,313, 5,141,966, 4,701,500 and 4,381,239, all of which are incorporated herein by reference. However, non-specific binding of proteins and low capacity are the major limitations to adsorbents employing the above-identified compounds.

Thiophilic compounds represent another class of pseudo-bioaffinity ligands. An adsorbent utilizing one type of thiophilic compound is disclosed by Porath et al. in *FEBS Lett.*, 185:306 (1985), which is incorporated herein by reference. This type of adsorbent is produced by reacting either a hydroxyl- or thiol-containing support first with divinyl sulfone and then with mercaptoethanol. The aforementioned adsorbent utilizes a salt-promoted approach to adsorb immunoglobulins. Elution of adsorbed immunoglobulins is effected by decreasing salt concentration and/or by modifying pH.

Another type of pseudobioaffinity adsorbent capable of adsorbing antibodies utilizes mercaptopyridine as its ligand. See Oscarsson et al., "Protein Chromatography with Pyridine- and Alkyl-Thioether-Based Agarose Adsorbents," *Journal of Chromatography*, 499:235–247 (1990), which is incorporated herein by reference. This type of adsorbent is generated, for example, by reacting mercaptopyridine with a properly activated solid support. The adsorbent thus formed is capable of adsorbing antibodies under high salt conditions.

Other pseudobioaffinity adsorbents utilizing thiophilic compounds are described in the following patents and publications, all of which are incorporated herein by reference: U.S. Pat. No. 4,897,467; published PCT application Ser. No. PCT/US89/02329; published European Patent Application No. 168,363; Oscarsson et al., "Thiophilic adsorbents for RIA and ELISA procedures," *Journal of Immunological Methods*, 143:143–149 (1991); and Porath et al., "A New King of 'Thiophilic' Electron-Donor-Acceptor Adsorbent," *Makromol. Chem., Macromol. Symp.*, 17:359–371 (1988).

The above-described thiophilic adsorbents provide a generally satisfactory means for purifying antibodies; however, in those cases in which the initial biological liquid is a protein rich solution, such as a serum or ascites, the non-specific binding by such adsorbents of a number of proteins other than the desired antibodies can be a problem. This problem of non-specific binding is the primary limitation of these thiophilic adsorbents.

Another group of low molecular weight ligands capable of selectively binding antibodies includes pentafluoropyridine and N-dimethylaminopyridine reacted with ethylene glycol, glycine or mercaptoethanol. See Ngo, *J. Chromatogr.*, 510:281 (1990), which is incorporated herein by reference. Adsorbents utilizing these materials can be used to isolate immunoglobulins in either high salt or low salt buffers or to isolate other types of proteins under low salt conditions. Elution of adsorbed proteins can be obtained by lowering pH.

Still other low molecular weight pseudobioaffinity ligands have been identified as being capable of selectively binding antibodies from egg yolk and other biological liquids. These ligands are special dyes. Elution of the bound antibodies from the ligands is achieved by special displacers.

All of the above-mentioned adsorbents utilizing low molecular weight pseudobioaffinity ligands are very attractive in terms of their low cost and their chemical and physical stability. However, their level of non-specific binding and/or their toxicity (should they, for example, contaminate a therapeutic antibody preparation intended for administration to humans) are too high, and their capacity for antibodies is too low to counterbalance the attractiveness of adsorbents utilizing Proteins A, G or L as specific antibody ligands.

SUMMARY OF THE INVENTION

Therefore, it is an object of the present invention to provide a novel pseudobioaffinity chromatography adsorbent which overcomes at least some of the limitations discussed above in connection with existing affinity and pseudobioaffinity chromatography adsorbents.

In furtherance of the above and other objects to be described or to become apparent below, a pseudobioaffinity chromatography adsorbent adapted for use in selectively adsorbing immunoglobulins is hereinafter provided, the adsorbent comprising in a first embodiment: (a) a solid support material; and (b) a ligand immobilized on the surface of the solid support material, said ligand being a compound of the formula

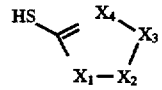

wherein each of $X_1$, $X_2$ and $X_3$ is selected from the group consisting of S, $SCH_3^+$, O, NH, $NCH_3$, $CH_2$ and $CR_1R_2$ wherein at least one of $R_1$ and $R_2$ is not hydrogen; wherein $X_4$ is selected from the group consisting of N, $NCH_3^+$, CH and CR wherein R is not hydrogen; and wherein at least two of $X_1$, $X_2$, $X_3$ and $X_4$ are neither $CH_2$, CH, CR nor $CR_1R_2$.

Alternatively, a pseudobioaffinity chromatography adsorbent adapted for use in selectively adsorbing immunoglobulins in accordance with a second embodiment of the invention comprises: (a) a solid support material; and (b) a ligand immobilized on the surface of the solid support material, said ligand being a compound of the formula

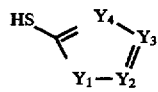

wherein $Y_1$ is selected from the group consisting of S, $SCH_3^+$, O, NH, $NCH_3$, $CH_2$ and $CR_1R_2$ wherein at least one of $R_1$ and $R_2$ is not hydrogen; wherein each of $Y_2$, $Y_3$ and $Y_4$ is selected from the group consisting of N, $NCH_3^+$, CH, and CR wherein R is not hydrogen; and wherein at least two of $Y_1$, $Y_2$, $Y_3$ and $Y_4$ are neither $CH_2$, CH, CR nor $CR_1R_2$.

The present invention is also directed to methods of making the aforementioned adsorbents and to methods of using the aforementioned adsorbents to perform affinity separations.

Additional objects, features and advantages of the present invention will be set forth in part in the description which follows, and in part will be obvious from the description or may be learned by practice of the invention. These embodiments will be described in sufficient detail to enable those skilled in the art to practice the invention, and it is to be understood that other embodiments may be utilized and that changes may be made without departing from the scope of the invention. The following detailed description is, therefore, not to be taken in a limiting sense, and the scope of the present invention is best defined by the appended claims.

DETAILED DESCRIPTION OF PREFERRED EMBODIMENTS

The present invention is directed to novel pseudobioaffinity chromatography adsorbents useful in the selective adsorption of a wide of range of immunoglobulins. The adsorbents of the present invention may also be used to selectively adsorb non-immunoglobulin proteins.

In accordance with the teachings of the present invention, the pseudobioaffinity chromatography adsorbents comprise (a) a solid support material; and (b) a ligand immobilized on the surface of the solid support material, the ligand being a mercapto five-membered heterocyclic ring of the type hereinafter described. In a first embodiment, said ligand has the structure represented below by compound I.

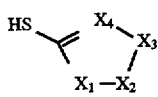

$$\text{(I)}$$

wherein each of $X_1$, $X_2$ and $X_3$ is selected from the group consisting of S, $SCH_3^+$, O, NH, $NCH_3$, $CH_2$ and $CR_1R_2$ wherein at least one of $R_1$ and $R_2$ is not hydrogen; wherein $X_4$ is selected from the group consisting of N, $NCH_3^+$, CH and CR wherein R is not hydrogen; and wherein at least two of $X_1$, $X_2$, $X_3$ and $X_4$ are neither $CH_2$, CH, CR nor $CR_1R_2$.

As indicated above, R, $R_1$ and $R_2$ can be virtually any functional group. Examples of R, $R_1$ and $R_2$, for illustrative purposes only, include substituted or unsubstituted alkyl, aryl, alkenyl, alkynyl, aralkyl, acyl, cycloalkyl, carboxyl, amino, aryloxy or alkoxy, halo, hydroxy, nitro, O, S, cyano or any of the functional groups disclosed in U.S. Pat. Nos. 4,223,036, 4,835,161 and 4,699,904, all of which are incorporated herein by reference.

For purposes of the present specification and claims, the particulars of $R_1$ and $R_2$ in $CR_1R_2$ of compound I may be either the same or different for two or more of $X_1$, $X_2$ and $X_3$. For example, $R_1$ and $R_2$ could be H and methyl, respectively, for $X_1$ and H and OH, respectively, for $X_2$. Alternatively, $R_1$ and $R_2$ could be, for example, ethyl and OH, respectively, for both $X_1$ and $X_2$.

Examples of compound I include mercaptothiazoline (e.g., 2-mercaptothiazoline) and 2-mercapto-5-thiazolidone.

In a second embodiment of the present invention, said ligand has the structure represented below by compound II.

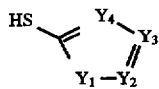

$$\text{(II)}$$

wherein $Y_1$ is selected from the group consisting of S, $SCH_3^+$, O, NH, $NCH_3$, $CH_2$ and $CR_1R_2$ wherein at least one of $R_1$ and $R_2$ is not hydrogen; wherein each of $Y_2$, $Y_3$ and $Y_4$ is selected from the group consisting of N, $NCH_3^+$, CH, and CR wherein R is not hydrogen; and wherein at least two of $Y_1$, $Y_2$, $Y_3$ and $Y_4$ are neither $CH_2$, CH, CR nor $CR_1R_2$.

R, $R_1$ and $R_2$ Of compound II can be virtually any functional group. Examples of R, $R_1$ and $R_2$, for illustrative purposes only, include substituted or unsubstituted alkyl, aryl, alkenyl, alkynyl, aralkyl, acyl, cycloalkyl, carboxyl, amino, aryloxy or alkoxy, halo, hydroxy, nitro, O, S, cyano or any of the functional groups disclosed in U.S. Pat. Nos. 4,223,036, 4,835,161 and 4,699,904, all of which are incorporated herein by reference.

For purposes of the present specification and claims, the particulars of R in CR of compound II may be either the same or different for two or more of $Y_2$, $Y_3$ and $Y_4$. For example, R could be methyl in the case of $Y_2$ and OH in the case of $Y_3$. Alternatively, R could be, for example, ethyl for both $Y_2$ and $Y_3$.

Examples of compound II include mercaptoimidazole (e.g., 2-mercaptoimidazole), mercaptoimidazoline, mercaptothiazole (e.g., 2-mercaptothiazole), mercaptotriazole (e.g., 3-mercapto-1,2,4-triazole and 5-mercapto-1,2,3-triazole), mercaptotetrazole (e.g., 5-mercapto-1,2,3,4-tetrazole), mercaptothiadiazole (e.g., 2-mercapto-1,3,4-thiadiazole) and mercaptomethylimidazole (e.g., N-methyl-2-mercaptoimidazole-a pharmaceutical known to be safe to humans).

The solid support material of the present adsorbents may be composed of polysaccharides, such as cellulose, starch, dextran, agar or agarose, or hydrophilic synthetic polymers, such as substituted or unsubstituted polyacrylamides, polymethacrylamides, polyacrylates, polymethacrylates, polyvinyl hydrophilic polymers, polystyrene, polysulfone or the like. Other suitable materials for use as the solid support material include porous mineral materials, such as silica, alumina, titania oxide, zirconia oxide and other ceramic structures. Alternatively, composite materials may be used as the solid support material. Such composite materials may be formed by the copolymerization of or by an interpenetrated network of two or more of the above mentioned entities. Examples of suitable composite materials include polysaccharide-synthetic polymers and/or polysaccharide-mineral structures and/or synthetic polymer-mineral structures, such as are disclosed in U.S. Pat. Nos. 5,268,097, 5,234,991 and 5,075,371, all of which are incorporated herein by reference.

The solid support material of the present invention may take the form of beads or irregular particles ranging in size from about 0.1 mm to 1000 mm in diameter, fibers (hollow or otherwise) of any size, membranes, flat surfaces ranging in thickness from about 0.1 mm to 1 mm thick and sponge-like materials with holes from a few μm to several mm in diameter.

Preferably, the ligands described above are chemically immobilized on the solid support material via a covalent bond formed between the mercapto group of the ligand and a reactive group present on the solid support. Reactive groups capable of reacting with the mercapto group of the present ligand include epoxy groups, tosylates, tresylates, halides and vinyl groups. Because many of the aforementioned solid support materials do not include one of the reactive groups recited above, bifunctional activating agents capable of both reacting with the solid support materials and providing the necessary reactive groups may be used. Examples of suitable activating agents include epichlorhydrin, epibromhydrin, dibromo- and dichloropropanol, dibromobutane, ethyleneglycol diglycidylether, butanediol diglycidylether, divinyl sulfone and the like.

By varying the concentration of the activating agent, the amount of immobilized ligand of the present invention can vary anywhere between a fraction of a μ-mole and several hundred μmoles per ml of solid matrix. Typically, a small quantity of ligand per unit volume results in a low separation capacity for immunoglobulins whereas a large quantity of ligand per unit volume results in an increased sorption capacity for immunoglobulins (and can induce nonspecific binding of proteins other than immunoglobulins).

The activating agents listed above have different chain lengths. Accordingly, by selecting a particular activating agent, one can control the distance between the solid support material and the immobilized ligand. Due to steric constraints, this distance between the ligand and the solid matrix can affect the adsorption characteristics of the final product both in terms of specificity and sorption capacity. Generally, more ligand can be immobilized on the solid support material in those instances in which the chain length is great than in those instances in which it is not.

Preparation of the adsorbents of the present invention may be effected in a manner similar to that by which conventional adsorbents have typically been prepared. More specifically, this may be done by reacting a solid support material of the type described above with an activating agent of the type described above under established conditions of concentration, temperature, pH, medium composition and time. Once activated, the support is then washed extensively in the established manner with solvents used to remove excess activating agent and/or activation byproducts therefrom. The washed, activated support is then contacted with ligands of the type described above under established conditions of concentration, pH, reaction temperature, reaction medium, time and agitation to produce an adsorbent which selectively adsorbs immunoglobulins from biological liquids contacted therewith.

Save for the one exception noted below, the adsorbents of the present invention may be used in the same manner that conventional adsorbents have been used. This comprises introducing the adsorbent into a chromatographic column and then washing the column with an appropriate aqueous solution of salts at a given pH. A biological solution containing the immunoglobulins wished to be isolated is then combined with salts (e.g., $Na_2SO_4$) and directly loaded into the column. The immunoglobulins present in the solution are captured by the adsorbent whereas the non-immunoglobulin proteins present in the solution and the remainder of the solution are recovered in the flowthrough. After an appropriate washing to eliminate non-specifically adsorbed macromolecules, the immunoglobulins are then desorbed by a pH shift and/or by changing the salt concentration. The isolated immunoglobulins are then neutralized.

The one exception alluded to above is that certain adsorbents of the present invention do not require that salt be added to the biological solution for the antibodies contained therein to adsorb to the ligand. This elimination of the need for salt is clearly advantageous in those instances in which the addition of salt is undesirable. Those adsorbents of the present invention for which salt need not be added (and, in fact, cannot be added in order for the adsorbent to function properly) are those which employ ligands of compounds I and II in which nitrogen atoms constitute the two or more heteroatoms of the five-membered heterocyclic ring. Examples of such ligands include 2-mercaptoimidazole, 3-mercapto-1,2,4-triazole, 5-mercapto-1,2,3-triazole, 5-mercapto-1,2,3,4-tetrazole and N-methyl-2-mercaptoimidazole.

The adsorbents of the present invention can be used to isolate a variety of different types of antibodies, such as native antibodies, chemically modified antibodies, bioengineered antibodies, antibody fragments and antibody conjugates containing enzymes, as well as various toxins, haptens and the like. In addition, the adsorbents of the present invention can be used to isolate antibodies from a variety of different biological liquids, such as hybridoma cell culture supernatants, plasma and plasma fractions, milk and milk fractions, ascitic fluids, fermentation broths and the like.

The adsorbents of the present invention represent a significant advancement in the art over adsorbents utilizing antibody-specific proteins, such as Protein A, Protein G, Protein L and the like. This is, in part, because the present adsorbents are stable against biological degradation, particularly degradation by hydrolytic enzymes. In addition, many of the ligands of the present adsorbents are commercially available chemicals of a current cost significantly lower than protein-based ligands. In addition, the present adsorbents can be treated with strong acidic and alkaline solutions which would otherwise be inappropriate with adsorbents utilizing protein ligands. Moreover, the present adsorbents can be treated with other cleaning agents, such as detergents, chaotropic salts and the like, without running the risk of adsorbent degradation or inactivation. Furthermore, heat treatment can be applied to the adsorbents of the present invention without modifying their capture efficiency or specificity.

As compared to existing pseudobioaffinity adsorbents, the present adsorbents are more specific and/or show higher sorption capacity for antibodies.

The following examples are illustrative only and should in no way limit the scope of the present invention:

EXAMPLE 1

Immobilization of 2-mercaptoimidazole on an Epoxy-Activated HYPERD™ Support 20 grams of epoxy-activated HYPERD™ silica oxide/polystyrene composite support with functionalized hydrogel filled pores (commercially available from BioSepra, Inc., Marlborough, Mass. and described in U.S. Pat. No. 5,268,097) were suspended in 100 ml of 35% 50 mM carbonate buffer, pH 8.6, and 65% ethanol, containing 5 mM 2-mercaptoimidazole and shaken for 16 hours. The slurry was filtered onto a sinter glass filter, washed with ethanol and drained. The modified HYPERD™ adsorbent was resuspended in 1 M ethanolamine, pH 10.5, shaken for 2.5 hours at 45° C., filtered and then washed with water. The beads were then resuspended in 2 M sodium acetate, and 2 ml of acetic anhydride was added over a period of one hour during shaking. The mixture was then shaken for an additional hour, filtered onto a sinter glass filter and washed with water until neutrality.

A chromatographic assay was then performed on the above-described adsorbent using 10 mM HEPES at pH 7.5. 1.5 ml of human serum was diluted three times with HEPES buffer and passed through a column of 1.2 ml gel volume. Elution was performed by changing the pH to 3.5 with citric acid buffer. Electrophoretic analysis of the elution fractions collected revealed that immunoglobulins constituted the major part of the adsorbed proteins, and the purity of the immunoglobulins was judged to be greater than 75%. The dynamic capacity of the modified gel by frontal analysis was 9.2 mg/ml at c/10 (i.e., 10% breakthrough) and 14.4 mg/ml at c/2 (i.e., 50% breakthrough) for human immunoglobulins at a flow rate of 120 cm/hr.

EXAMPLE 2

Immobilization of 2-aminoimidazole on an Epoxy-Activated HYPERD™ Support

An adsorbent similar to that synthesized in Example 1 was prepared, the only difference being that 2-aminoimidazole was substituted for 2-mercaptoimidazole. An evaluation of the dynamic capacity of the adsorbent was performed using frontal analysis and showed that the 2-aminoimidazole adsorbent had a dynamic capacity of 1.5 mg/ml at c/10 and 2.5 mg/ml at c/2 for human immunoglobulins at a flow rate of 120 cm/hr.

Comparing the results of Examples 1 and 2, it can be seen that, when a sulfur group (mercaptoimidazole) is replaced by a nitrogen group (aminoimidazole), the sorption capacity and capture efficiency are dramatically decreased.

EXAMPLE 3

Immobilization of 2-mercaptothiazole on an Epoxy-Activated HYPERD™ Support

An adsorbent similar to that synthesized in Example 1 was prepared, the only difference being that 2-mercaptothiazole was substituted for 2-mercaptoimidazole. A chromatographic assay was performed using 10 mM HEPES and 500 mM sodium sulfate at pH 7.5. 1.5 ml of human serum was passed through a column of 4.6 ml gel volume, and elution was performed by changing the pH to 3.5 with citric acid buffer.

Electrophoretic analysis of the elution fractions collected revealed that immunoglobulins constituted the major part of the adsorbed proteins, and the purity of the immunoglobulins was judged to be greater than 85%. The capacity of the modified gel by frontal analysis was determined to be 6.2 mg/ml at c/10 and 7.9 mg/ml at c/2 at a flow rate of 120 cm/hr.

EXAMPLE 4

Immobilization of 2-mercaptothiazoline on an Epoxy-Activated HYPERD™ Support

An adsorbent similar to that synthesized in Example 1 was prepared, the only difference being that 2-mercaptothiazoline was substituted for 2-mercaptoimidazole. A chromatographic assay was performed using 10 mM HEPES and 500 mM sodium sulfate at pH 7.5. 1.5 ml of human serum was passed through a column of 4.6 ml gel volume, and elution was performed by changing the pH to 3.5 with citric acid buffer.

Electrophoretic analysis of the elution fractions collected revealed that immunoglobulins constituted the major part of the adsorbed proteins, and the purity of the immunoglobulins was judged to be greater than 85%. The capacity of the modified gel by frontal analysis was determined to be 6.2 mg/ml at c/10 and 7.7 mg/ml at c/2 at a flow rate of 120 cm/hr.

EXAMPLE 5

Immobilization of 3-mercapto-1,2,4-triazole on an Epoxy-Activated HYPERD™ Support An adsorbent similar to that synthesized in Example 1 was prepared, the only difference being that 3-mercapto-1,2,4-triazole was substituted for 2-mercaptoimidazole. Using the same sort of assay described above in Example 1, the capacity of the modified gel for pure human antibodies was determined by frontal analysis to be 1.5 mg/ml at c/10 and 8.1 mg/ml at c/2 at a flow rate of 146 cm/hr and an adsorption buffer containing 10 mM HEPES at pH 7.

EXAMPLE 6

Immobilization of 2-mercapto-1,3,4-thiadiazole on an Epoxy-Activated HYPERD™ Support An adsorbent similar to that synthesized in Example 1 was prepared, the only difference being that 2-mercapto-1,3,4-thiadiazole was substituted for 2-mercaptoimidazole. Using the same sort of assay described above in Example 1, the capacity of the modified gel for pure human antibodies was determined by frontal analysis to be 9.1 mg/ml at c/10 and 11.2 mg/ml at c/2 at a flow rate of 140 cm/hr in an adsorption buffer containing 10 mM HEPES and 750 mM sodium sulfate at pH 7.

EXAMPLE 7

Immobilization of 2-mercapto-5-thiazolidone on an Epoxy-Activated HYPERD™ Support An adsorbent similar to that synthesized in Example 1 was prepared, the only difference being that 2-mercapto-5-thiazolidone was substituted for 2-mercaptoimidazole. Using the same sort of assay described above in Example 1, the capacity of the modified gel for pure human antibodies was determined by frontal analysis to be 9 mg/ml at c/10 and 12.2 mg/ml at c/2 at a flow rate of 134 cm/hr in an adsorption buffer containing 10 mM HEPES and 750 mM sodium sulfate at pH 7

EXAMPLE 8

Immobilization of 2-mercaptothiazoline on a Vinyl-Activated HYPERD™ Support 15 grams of amino-HYPERD™ (prepared by amination by reacting the epoxy-activated HYPERD™ of Example 1 with ethylene diamine) were suspended in 80 ml of a mixture containing 35% 100 mM carbonate buffer, pH 9.5, and 65% ethanol. To this slurry was added 7 ml of divinyl sulfone, and the slurry was shaken for 20 hours at 45° C. The slurry was filtered, washed with ethanol and dried. The beads were resuspended in 75 ml of a mixture of 35% 50 ml carbonate buffer, pH 8.6, and 65% ethanol containing 5 mM 2-mercaptothiazoline and then shaken for 24 hours at 45° C. The slurry was then filtered onto a sinter glass filter, washed with ethanol and dried. The modified HYPERD™ support was then resuspended in 100 ml of a solution containing 1 M ethanolamine, pH 10.5, shaken for 2.5 hours at 45° C., filtered and washed with water.

A chromatographic assay was performed using 10 mM HEPES and 500 mM sodium sulfate at pH 7.5. 1.5 ml of human serum was passed through a column of 4.6 ml gel volume, and elution was performed by changing the pH to 2.5 with citric acid buffer. Electrophoretic analysis of the elution fractions collected revealed that immunoglobulins constituted the major part of the adsorbed proteins, and the purity of the immunoglobulins was judged to be greater than 85%. The capacity of the modified gel was determined by frontal analysis to be 11.8 mg/ml at c/10 and 14.4 mg/ml at c/2 at a flow rate of 120 cm/hr.

EXAMPLE 9

Immobilization of 2-mercaptothiazole on a Bromo-Activated HYPERD™ Support 5 grams of bromo-activated HYPERD™ were suspended in 25 ml of a mixture of 35% 50 mM carbonate buffer, pH 8.6, and 65% ethanol containing 600 mg of 2-mercaptothiazole. The slurry was rotated, head over head, for 20 hours at room temperature and then filtered onto a sinter glass filter, washed and drained. The slurry was then resuspended in an aqueous solution of 1 M ethanolamine at pH 10.5 and rotated, head over head, for two hours at room temperature. The slurry was then filtered, washed with water until neutrality and then resuspended in 2 M sodium acetate. 1 ml of acetic anhydride was then added over the course of one hour. The slurry was then rotated for an additional hour and then filtered onto a sinter glass filter, washed to neutrality and drained.

The modified gel was then evaluated with pure human IgG. Frontal analysis of the modified gel showed a dynamic capacity of 2.2 mg/ml at c/10 and 7.8 mg/ml at c/2 at a flow rate of 160 cm/hr using 10 mM HEPES and 500 mM $Na_2SO_4$ at pH 7.0.

EXAMPLE 10

Immobilization of 2-mercaptothiazole on Epoxy-SEPHAROSE CL-6B Support 2.5 ml of Epoxy-SEPHAROSE CL-6B support (epoxy-activated agarose beads with an epoxy content of 10–12 µM/ml of gel; commercially available from Pharmacia Biotech, Piscataway, N.J.) were suspended in 15 ml of a mixture of 35% 50 mM carbonate buffer, pH 8.6, and 65% ethanol containing 600 mg of 2-mercaptothiazole. The slurry was rotated, head over head, for 20 hours and then filtered onto a glass filter, washed and drained. The agarose beads were then resuspended in an aqueous solution of 1 M ethanolamine at pH 10.5 and rotated, head over head, for two hours at room temperature. The slurry was then filtered and washed with water until neutrality and then resuspended in 2 M sodium acetate. 1 ml of acetic anhydride was then added over the course of one hour. The slurry was then rotated for an additional hour, filtered onto a sinter glass filter, washed to neutrality and drained.

The modified gel was evaluated with pure human IgG. Frontal analysis of the modified gel showed a dynamic capacity of 5.4 mg/ml at c/10 and 24.2 mg/ml at c/2 at a flow rate of 75 cm/hr using 10 mM HEPES and 500 mM $Na_2SO_4$ at pH 7.0.

EXAMPLE 11

Immobilization of 2-mercapto-1,3,4-thiadiazole on EUPERGIT® Support 20 g of EUPERGIT® support (a copolymer of methacrylamide, N, N-methylenebis(methacrylamide) and a component containing an active oxirane group; commercially available from Rohm Pharma, Darmstadt, Germany) are suspended in 50 ml of 50% 50 mM carbonate buffer, pH 8.6, and 50% ethanol. To this suspension are added 50 ml of ethanol containing 5 mM of 2-mercapto-1,3,4-thiadiazole, and the slurry is shaken for 16 hours. The slurry is then filtered, washed with 50 mM carbonate buffer at pH 8.6/ ethanol (1:1) and drained under vacuum. The modified support is then saturated with ethanolamine as described in Example 1 and tested for its ability to separate antibodies from human plasma. Its sorption capacity is also checked by frontal analysis using pure human IgG and is expected to be within ±10% of that disclosed for the adsorbent in Example 6.

EXAMPLE 12

Immobilization of 2-mercapto-1,3,4-thiadiazole on Epoxy-FRACTOGEL Support 20 g of Epoxy-FRACTOGEL support (epoxy-activated polymethacrylate support; commercially available from E. Merck, Wakefield, R.I.) are suspended in 50 ml of 50% of 50 mM carbonate buffer, pH 8.6, and 50% ethanol. To this suspension are added 50 ml of ethanol containing 5 mM of 2-mercapto-1,3,4-thiadiazole, and the slurry is shaken for 16 hours. The slurry is then filtered, washed with 50 mM carbonate buffer at pH 8.6/ethanol (1:1) and drained under vacuum. The modified support is then saturated with ethanolamine as described in Example 1 and tested for its ability to separate antibodies from human plasma. Its sorption capacity is also checked by frontal analysis using pure human IgG and is expected to be within ±10% of that disclosed for the adsorbent in Example 6.

EXAMPLE 13

Immobilization of 3-mercapto-1,2,4-triazole on SPHEROX® Support 20 g of the commercially-available SPHERODEX® support (dextran-silica composite support available from BioSepra, Inc., Marlborough, Mass.) are suspended in 70 ml of deionized water. Under agitation, 10 ml of ethyleneglycoldiglycidylether and 30 ml of 1M sodium hydroxide containing 200 mg sodium borohydride are added. The mixture is shaken for 16 hours at room temperature and then rapidly washed with deionized water until neutrality. The epoxy-activated SPHERODEX® support is then reacted with 3-mercapto-1,2,4-triazole as described in Example 1 (without the last acetylation step) and tested for its ability to separate antibodies from human plasma. Its sorption capacity is also checked by frontal analysis using pure human IgG and is expected to be within ±10% of that disclosed for the adsorbent in Example 5.

EXAMPLE 14

Purification of Imunoglobulins from Bovine Colostrum on 2-mercaptoimidazole

Bovine colostrum was diluted 1:1 with adsorption buffer (10 mM HEPES, pH 7.3) and filtered. Adsorption was performed on a 5.9 ml column at a flow rate of 120 cm/hr. Elution was performed by 200 mM sodium dihydrogen phosphate, pH 4.25. Electrophoretic analysis revealed that the immunoglobulins eluted were greater than 80% pure.

The embodiments of the present invention recited herein are intended to be merely exemplary and those skilled in the art will be able to make numerous variations and modifications to it without departing from the spirit of the present invention. All such variations and modifications are intended to be within the scope of the present invention as defined by the claims appended hereto.

What is claimed is:

1. A method of performing affinity separations of an immunoglobulin to be separated from a biological liquid, said method comprising:

(a) contacting the biological liquid containing the immunoglobulin with a pseudobioaffinity chromatography adsorbent comprising:
      (i) a solid support material; and
      (ii) a ligand immobilized on the surface of said solid support material, said ligand being a compound of the formula

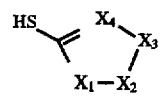

wherein:

each of $X_1$, $X_2$ and $X_3$ is selected from the group consisting of S, $SCH_3^+$, O, NH, $NCH_3$, and $CR_1R_2$;

$X_4$ is selected from the group consisting of N, $NCH_3^+$, and CR;

R, $R_1$ and $R_2$ are independently chosen from the group consisting of H, alkyl, substituted alkyl, aryl, alkenyl, alkynyl, aralkyl, acyl, cycloalkyl, carboxyl, amino, aryloxy, halo, hydroxy, nitro, O, S, and cyano;

with the proviso that at least two of $X_1$, $X_2$, $X_3$ and $X_4$ are neither CR nor $CR_1R_2$; said biological liquid having added thereto an amount of salt sufficient to permit said immunoglobulin to bind to said ligand; and (b) removing said biological liquid from contact with said pseudobioaffinity chromatography adsorbent, whereby separation of said immunoglobulin from said biological liquid is effected.

2. The method as claimed in claim 1 wherein each of $X_1$, $X_2$ and $X_3$ is selected from the group consisting of NH, $NCH_3$ and $CR_1R_2$ and wherein said amount of salt is zero.

3. A method of performing affinity separations of an immunoglobulin to be separated from a biological liquid, said method comprising:
  (a) contacting the biological liquid containing the immunoglobulin with a pseudobioaffinity chromatography adsorbent comprising:
    (i) a solid support material; and
    (ii) a ligand immobilized on the surface of the solid support material, said ligand being a compound of the formula

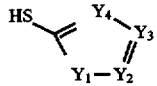

wherein:

$Y_1$ is chosen from the group consisting of S, $SCH_3^+$, O, NH, $NCH_3$, and $CR_1R_2$;

each of $Y_2$, $Y_3$ and $Y_4$ is selected from the group consisting of N, $NCH_3^+$ and CR; each of R, $R_1$ and $R_2$ is selected from the group consisting of H, alkyl, substituted alkyl, aryl, alkenyl, alkynyl, aralkyl, acyl, cycloalkyl, carboxyl, amino, aryloxy, halo, hydroxy, nitro, O, S, and cyano;

with the proviso that at least two of $Y_1$, $Y_2$, $Y_3$ and $Y_4$ are neither CR nor $CR_1R_2$; said biological liquid having added thereto an amount of salt sufficient to permit said immunoglobulin to bind to said ligand; and (b) removing said biological liquid from contact with said pseudobioaffinity chromatography adsorbent, whereby separation of said immunoglobulin from said biological liquid is effected.

4. The method as claimed in claim 3 wherein $Y_1$ is selected from the group consisting of NH, $NCH_3$ and $CR_1R_2$ and wherein said amount of salt is zero.

* * * * *